United States Patent
Chen et al.

(10) Patent No.: US 10,130,569 B2
(45) Date of Patent: Nov. 20, 2018

(54) DENTIFRICE COMPOSITIONS HAVING DENTAL PLAQUE MITIGATION OR IMPROVED FLUORIDE UPTAKE

(71) Applicant: The Procter & Gamble Company, Cincinnati, OH (US)

(72) Inventors: Haijing Chen, Beijing (CN); Ross Strand, Beijing (CN); Donald James White, Jr., Fairfield, OH (US); Hongmei Yang, Beijing (CN)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 14/634,969

(22) Filed: Mar. 2, 2015

(65) Prior Publication Data
US 2015/0328089 A1    Nov. 19, 2015

(51) Int. Cl.
| | |
|---|---|
| *A61K 8/19* | (2006.01) |
| *A61K 8/21* | (2006.01) |
| *A61K 8/25* | (2006.01) |
| *A61K 8/37* | (2006.01) |
| *A61K 8/73* | (2006.01) |
| *A61K 8/46* | (2006.01) |
| *A61K 8/24* | (2006.01) |
| *A61Q 11/00* | (2006.01) |

(52) U.S. Cl.
CPC .................. *A61K 8/19* (2013.01); *A61K 8/21* (2013.01); *A61K 8/24* (2013.01); *A61K 8/25* (2013.01); *A61K 8/37* (2013.01); *A61K 8/73* (2013.01); *A61K 8/731* (2013.01); *A61Q 11/00* (2013.01); *A61K 8/463* (2013.01); *A61K 2800/28* (2013.01); *A61K 2800/30* (2013.01); *A61K 2800/48* (2013.01); *A61K 2800/92* (2013.01)

(58) Field of Classification Search
USPC ...................................... 424/51, 52, 55, 675
See application file for complete search history.

(56) References Cited

U.S. PATENT DOCUMENTS

| | | | |
|---|---|---|---|
| 1,526,940 A * | 2/1925 | Staegemann | A61K 8/466 424/55 |
| 3,119,743 A * | 1/1964 | Ericsson | A61K 8/19 424/52 |
| 4,701,319 A | 10/1987 | Woo | |
| 4,828,849 A | 5/1989 | Lynch et al. | |
| 5,310,543 A | 5/1994 | Dawson | |
| 5,624,906 A * | 4/1997 | Vermeer | A61K 8/60 514/23 |
| 6,106,811 A | 8/2000 | Gibbs | |
| 6,159,446 A | 12/2000 | Randive et al. | |
| 6,669,928 B1 * | 12/2003 | Gurol | A61K 8/19 424/49 |
| 6,696,045 B2 | 2/2004 | Yue et al. | |
| 6,855,325 B1 | 2/2005 | Yvin et al. | |
| 8,007,771 B2 | 8/2011 | Ramji et al. | |
| 2003/0072721 A1 | 4/2003 | Riley et al. | |
| 2004/0120902 A1 | 6/2004 | Wernett et al. | |
| 2004/0131560 A1 | 7/2004 | Corcoran et al. | |
| 2004/0161388 A1 * | 8/2004 | Liu | A61K 8/19 424/49 |
| 2006/0159631 A1 | 7/2006 | Buch et al. | |
| 2007/0009447 A1 | 1/2007 | Gadkari et al. | |
| 2007/0231278 A1 | 10/2007 | Lee et al. | |
| 2009/0269287 A1 | 10/2009 | Berta | |
| 2013/0064779 A1 | 3/2013 | Yamane et al. | |
| 2014/0377191 A1 | 12/2014 | Gadkari et al. | |
| 2015/0050322 A1 | 2/2015 | Ashcroft et al. | |

FOREIGN PATENT DOCUMENTS

| | | |
|---|---|---|
| KR | 2002/0054045 A | 7/2002 |
| KR | 2012/0042399 A | 5/2012 |
| WO | WO 2007/122146 A1 | 11/2007 |

OTHER PUBLICATIONS

Pearce, et al. "The Effect of pH, Temperature and Plaque Thickness on the Hydrolysis of Monofluorophosphate in Experimental Dental Plaque", Caries Research, vol. 37, pp. 178-184, Feb. 1, 2003.
PCT Supplementary International Search Report, dated Feb. 26, 2016, 11 Pages.

* cited by examiner

*Primary Examiner* — Walter E Webb
(74) *Attorney, Agent, or Firm* — James E. Oehlenschlager; Alexandra S. Anoff

(57) ABSTRACT

Dentifrice compositions with high water, a calcium-containing abrasive, an alkaline pH and minimal or nil amounts of polyols, such as PEG humectants, provide improved anti-plaque benefits.

17 Claims, 1 Drawing Sheet

| Components: (Weight Percentage) | Ex 1# | Ex 2# | Ex 3# | Ex 4# Control A | Ex 5# Control B | Ex 6# Control C | Ex 7# Control D | Ex 8# Positive Control |
|---|---|---|---|---|---|---|---|---|
| Water | 58.77 | 55.77 | 58.26 | 42.61 | 41.37 | 13.87 | 65.37 | 51.37 |
| Sodium Monofluorophosphate | 1.1 | 1.1 | 1.1 | 1.1 | 1.1 | 1.1 | 0.8 | 0 |
| Mono Sodium Phosphate | 0.08 | 0.08 | 0.08 | 0.08 | 0.08 | 0.08 | 0 | 0 |
| Tetra Sodium Pyrophosphate | 0.6 | 0.6 | 0.6 | 0.06 | 0.6 | 0.6 | 0 | 0 |
| Tri Sodium Phosphate | 0.42 | 0.42 | 0.42 | 0.42 | 0.42 | 0.42 | 0 | 0 |
| Saccharin | 0.25 | 0.25 | 0.25 | 0.25 | 0.25 | 0.25 | 0.48 | 0.4 |
| Sodium Carboxymethyl Cellulose | 0.91 | 0.91 | 0.91 | 0.91 | 0.91 | 0.91 | 0.4 | 0 |
| Carrageenan-Iota | 1.2 | 1.2 | 1.2 | 1.2 | 1.2 | 1.2 | 2 | 0.8 |
| Thickening Silica | 2.62 | 2.62 | 2.62 | 2.62 | 2.62 | 2.62 | 3 | 0 |
| Silica Abrasive ZEODENT™ 119 | 0 | 0 | 0 | 0 | 0 | 0 | 0 | 2 |
| Calcium Carboante | 32 | 32 | 32 | 32 | 32 | 32 | 25 | 0 |
| PEG-600 | 0 | 2 | 0 | 0 | 0 | 0 | 0 | 0 |
| Sorbitol | 0 | 0 | 0 | 16.8 | 17.5 | 0 | 0 | 38.8 |
| Glycerin | 0 | 0 | 0 | 0 | 0 | 45 | 0 | 0 |
| Sodium Lauryl Sulfate | 1.1 | 2.1 | 1.61 | 1.1 | 1.1 | 1.1 | 2.1 | 1.1 |
| Methyl Paraben | 0.05 | 0.05 | 0.05 | 0 | 0 | 0 | 0 | 0 |
| Propyl Paraben | 0.05 | 0.05 | 0.05 | 0 | 0 | 0 | 0 | 0 |
| Flavor | 0.85 | 0.85 | 0.85 | 0.85 | 0.85 | 0.85 | 0.85 | 1 |
| Stannous Fluoride | 0 | 0 | 0 | 0 | 0 | 0 | 0 | 0.45 |
| Stannous Chloride | 0 | 0 | 0 | 0 | 0 | 0 | 0 | 1.5 |
| Hydroxyethyl Cellulose | 0 | 0 | 0 | 0 | 0 | 0 | 0 | 0.5 |
| Sodium Gluconate USP | 0 | 0 | 0 | 0 | 0 | 0 | 0 | 2.08 |
| Total: | 100% | 100% | 100% | 100% | 100% | 100% | 100% | 100% |

DENTIFRICE COMPOSITIONS HAVING DENTAL PLAQUE MITIGATION OR IMPROVED FLUORIDE UPTAKE

CROSS REFERENCE TO RELATED APPLICATION

This application claims the benefit of Application No. CN2014/077535, filed May 15, 2014.

FIELD OF THE INVENTION

The present invention relates to dentifrice compositions having dental plaque mitigation properties or improved fluoride uptake.

BACKGROUND OF THE INVENTION

Dentifrice compositions are well known for dental and oral hygiene care. High water (e.g., >45 wt %) and high carbonate (e.g., >25 wt %) formulation chassis are cost effective for many markets and consumers. Dental plaque is a sticky, colorless deposit of bacteria that is constantly forming on the tooth surface. Saliva, food and fluids combine to produce these deposits that collect where the teeth and gums meet. Plaque buildup is the primary factor in poor oral health that can lead to caries and periodontal (gum) disease, including gingivitis. One way dentifrice compositions help prevent and control plaque is by leveraging anti-bacterial agents, however, the disadvantage and formulation challenge is the unintended reactivity of anti-bacterial agents with formulation ingredients and environment of containing calcium carbonate matrix. This may include oxidative degradation, hydrolysis, adsorption or precipitation of oxy-hydroxide species, any of which can impact the bio-availability of the anti-bacterial agent. There is a continuing need to provide such formulations that help prevent plaque formation on teeth and/or minimize the use of antimicrobial agents, particularly in high water and high carbonate dentifrice formulation chassis.

SUMMARY OF THE INVENTION

A surprising discovery is the role of pH in high water and high carbonate dentifrice formulations. Specifically, an alkaline pH, i.e., higher than 7.8, contributes to anti-plaque or plaque mitigation benefits to the dentifrice compositions described herein. The alkaline pH helps to provide an inhospitable environment for many types of bacteria. Yet furthermore, in those dentifrice formulations containing sodium monofluorophosphate as a fluoride ion source, these alkaline compositions exhibit enhanced fluoride ion stability and efficacy.

One aspect of the invention provides for a dentifrice composition comprising: (a) 45% to 75% water, preferably 50% to 60% water, by weight of the composition; (b) 25% to 50%, preferably 27% to 47%, preferably 27% to 37% of a calcium-containing abrasive by weight of the composition, preferably wherein the calcium-containing abrasive comprises calcium carbonate; and (c) a pH greater than 7.8, preferably greater than 8.3, more preferably greater than 8.5, yet more preferably at or greater than 9. Another aspect of the invention is based on yet another surprising discovery that minimizing or removing the use of formulation ingredients that act as a potential source of nutrition for bacteria can help prevent or mitigate plaque formation. For example, some polyols and saccharide-based ingredients may be used by some bacteria as food sources thereby potentially contributing to plaque formation. However, many of these ingredients are used to impart desirable properties to dentifrice formulations. For example, polyols like glycerin and sorbitol are traditionally used as humectants. The use of carrageenan is reported as a thickening or binding agent and replacing some traditional humectants. See US 2009/0269287 A1. However, carrageenan is a polysaccharide (i.e., made up of repeating galactose units and 3,6 anhydrogalactose (3,6-AG)).

An advantage of the present advantage is that it provides dentifrice formulations with desirable rheology properties, i.e. an appealing appearance and proportionate dispersion during brushing while minimizing the use of polyols and saccharide-based ingredients that can act as bacteria food sources. Accordingly one aspect of the invention provides a high water and high carbonate dentifrice formulations comprising a thickening agent system that minimizes the level of carrageenan and contains a low or nil level of traditional humectants.

Furthermore, the reduction or elimination of the polyols from the formulation can reduce the interference from hygroscopic effects in the gel phase of plaque.

Yet another advantage of the invention is to save costs by minimizing the levels of relatively expensive thickening agents such as carrageenan and humectants. Another aspect of the invention provides for dentifrice composition comprising: (a) 45% to 75% water, preferably from 50% to 60% water, by weight of the composition; (b) 25% to 50%, preferably from 27% to 47%, more preferably from 27% to 37% of a calcium-containing abrasive by weight of the composition, preferably wherein the calcium-containing abrasive comprises calcium carbonate; (c) from 0.01% to less than 1.4%, preferably from 0.1% to 1.3%, more preferably from 0.5% to 1.3% of a carrageenan by weight of the composition; and (d) greater than 0.4% to 2%, preferably from 0.5% to 1.8%, more preferably from 0.6% to 1.8% of a carboxymethyl cellulose (CMC) by weight of the composition.

Yet another surprising observation is that higher surfactant levels (e.g., >2 wt %) in high water, high carbonate, and low or nil humectant formulations can lead to physical instability. The use of polyethylene glycol (PEG), specifically PEG-600, provides physical stability to such formulations without the negatives associated with other potential ingredients. Accordingly, another aspect of the invention provides for a dentifrice composition comprising: (a) 45% to 75% water, preferably from 50% to 60% water, by weight of the composition; (b) 25% to 50%, preferably from 27% to 47%, more preferably from 27% to 37% of a calcium-containing abrasive by weight of the composition, preferably wherein the calcium-containing abrasive comprises calcium carbonate; (c) 2% to 9% of a surfactant, preferably wherein the surfactant is an anionic surfactant, more preferably wherein the anionic surfactant is sodium lauryl sulfate; (d) 0.1% to 5%, preferably from 1% to 4%, of polyethylene glycol (PEG) by weight of the composition, preferably wherein the PEG has an average molecular weight range from 100 Daltons to 1,600 Daltons, preferably from 200 Daltons to 1,000 Daltons; and (e) an alkaline pH.

Yet still another surprising observation is that lower or nil polyol (e.g., glycerin and sorbitol) provides better fluoride uptake as compared to those formulations that have high levels of such polyols. Accordingly, one aspect of the invention provides for a dentifrice composition comprising: (a) 45% to 75% water, preferably 50% to 60% water, by weight of the composition; (b) 25% to 50%, preferably 27% to 47%, preferably 27% to 37% of a calcium-containing abrasive by weight of the composition, preferably wherein the calcium-containing abrasive comprises calcium carbonate; (c) pH greater than 7.8, preferably greater than 8.2, more preferably greater than 8.5, yet more preferably the pH at or greater than 9, alternatively the pH is from 9 to 12; and (d) wherein the composition is free or substantially free of a humectant, wherein the humectant is glycerol or sorbitol.

Yet another aspect of the invention provides for a dentifrice composition comprising: (a) 45% to 75% water, preferably 50% to 60% water, by weight of the composition; (b) 25% to 50%, preferably 27% to 47%, preferably 27% to 37% of a calcium-containing abrasive by weight of the composition, preferably wherein the calcium-containing abrasive comprises calcium carbonate; (c) pH greater than 7.8, preferably greater than 8.2, more preferably greater than 8.5, yet more preferably the pH at or greater than 9, alternatively the pH is from 9 to 12; and (d) (d) wherein the composition is free or substantially free of a polyol.

Yet another aspect of the invention provides a method of treating tooth enamel comprising the step of brushing teeth with a dentifrice composition of the present invention.

Yet still another aspect of the invention provides a method preventing or mitigating plaque formation on tooth enamel comprising the step of brushing teeth with a dentifrice composition of the present invention.

These and other features, aspects, and advantages of the present invention will become evident to those skilled in the art from the detailed description which follows.

BRIEF DESCRIPTION OF THE DRAWINGS

FIG. 1 shows formulation components for Examples 1-8, wherein Examples 4-8 are control formulations (A-E, respectively).

DETAILED DESCRIPTION OF THE INVENTION

Definitions

The term "orally acceptable carrier" as used herein means a suitable vehicle or ingredient, which can be used to form and/or apply the present compositions to the oral cavity in a safe and effective manner.

The term "comprising" as used herein means that steps and ingredients other than those specifically mentioned can be added. This term encompasses the terms "consisting of" and "consisting essentially of" The compositions of the present invention can comprise, consist of, and consist essentially of the essential elements and limitations of the invention described herein, as well as any of the additional or optional ingredients, components, steps, or limitations described herein.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount" means at least 0.01% of the material, by weight of the composition, alternatively at least 0.1%.

The term "dentifrice" as used herein means paste, gel, powder, tablets, or liquid formulations, unless otherwise specified, that are used to clean the surfaces of the oral cavity. The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Water

The compositions of the present invention comprise herein from 45% to 75%, by weight of the composition of water. In one embodiment, the composition includes from 40% to 70%, alternatively from 45% to 65%, alternatively from 40% to 60%, alternatively from 50% to 70%, alternatively from 50% to 60%, alternatively from 45% to 55%, alternatively from 55% to 65%, alternatively from 50% to 60%, alternatively about 55%, alternatively combinations thereof, of water by weight of the composition. The water may be added to the formulation and/or may come into the composition from the inclusion of other ingredients. Preferably the water is USP water.

Calcium-Containing Abrasive

The compositions of the present invention comprise from 25% to 50% by weight of a calcium-containing abrasive, wherein the calcium-containing abrasive is selected from the group consisting of calcium carbonate, dicalcium phosphate, tricalcium phosphate, calcium orthophosphate, calcium metaphosphate, calcium polyphosphate, calcium oxyapatite, sodium carbonate, and combinations thereof. In a preferred embodiment, the composition comprises from 25% to 60%, more preferably from 25% to 50%, even more preferably from 25% to 40%, yet even more preferably from 26% to 39%, alternatively from 27% to 47%, alternatively from 27% to 37%, alternatively from 30% to 35%, alternatively from 30% to 34%, alternatively combinations thereof, of a calcium-containing abrasive by weight of the composition.

In one embodiment, the calcium-containing abrasive is calcium carbonate. In a preferred embodiment, the calcium-containing abrasive is selected from the group consisting of fine ground natural chalk, ground calcium carbonate, precipitated calcium carbonate, and combinations thereof.

Fine ground natural chalk (FGNC) is one of the more preferred calcium-containing abrasives useful in the present invention. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling. One example of natural chalk is described in WO 03/030850 having a medium particle size of 1 to 15 µm and a BET surface area of 0.5 to 3 $m^2/g$. The natural calcium carbonate may have a particle size of 325 to 800 mesh, alternatively a mesh selected from 325, 400 600, 800, or combinations thereof; alternatively the particle size is from 0.1 to 30 microns, or from 0.1 to 20 microns, or from 5 to 20 microns.

In one embodiment, the composition of the present invention is free or substantially free of silicate.

PEG

The compositions of the present invention may comprise polyethylene glycol (PEG), of various weight percentages of the composition as well as various ranges of average molecular weights. In one aspect of the invention, the compositions have from 0.1% to 15%, preferably from 0.2% to 12%, more preferably from 0.3% to 10%, yet more preferably from 0.5% to 7%, alternatively from 1% to 5%, alternatively from 1% to 4%, alternatively from 1% to 2%, alternatively from 2% to 3%, alternatively from 4% to 5%, or combinations thereof, of PEG by weight of the composition. In another aspect of the invention, the PEG is one having a range of average molecular weight from 100 Daltons to 1600 Daltons, preferably from 200 to 1000, alternatively from 400 to 800, alternatively from 500 to 700 Daltons, alternatively combinations thereof. PEG is a water soluble linear polymer formed by the addition reaction of ethylene oxide to an ethylene glycol equivalent having the general formula: $H-(OCH_2CH_2)_n-OH$. One supplier of PEG is Dow Chemical Company under the brandname of CARBOWAX™.

Sweetener

The oral care compositions herein may include a sweetening agent. These include sweeteners such as saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in oral compositions at levels of from 0.005% to 5%, by weight of the composition, alternatively 0.01% to 1%, alternatively from 0.1% to 0.5%, alternatively combinations thereof.

Fluoride Ion Source

The compositions may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from about 0.0025% to about 5% by weight of the composition, alternatively from about 0.005% to about 2.0% by weight of the composition, to provide anti-caries effectiveness. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate, and zinc fluoride. In one embodiment, the dentifrice composition contains a fluoride source selected from stannous fluoride, sodium fluoride, and mixtures thereof. In one embodiment, the fluoride ion source is sodium monofluorophosphate, and wherein the composition comprises 0.0025% to 2% of the sodium monofluorophosphate by weight of the composition, alternatively from 0.5% to 1.5%, alternatively from 0.6% to 1.7%, alternatively combinations thereof. In another embodiment, the composition comprises from 0.0025% to 2% of a fluoride ion source by weight of the composition.

pH

The pH of the dentifrice composition may be greater than pH 7.8, preferably greater than pH 8.3, or from pH 8 to 13, or from pH 8.4 to 13, or more preferably from pH 9 to 12, alternatively greater than pH 8.5, alternatively greater than pH 9, alternatively from pH 9 to 11, alternatively from pH 9 to 10, or combinations thereof.

A method for assessing pH of dentifrice is described. pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body—VWR #34104-834/Orion #8172BN or VWR#10010-772/Orion #8172BNWP; Epoxy body—VWR #34104-830/Orion #8165BN or VWR#10010-770/Orion #8165BNWP; Semi-micro, epoxy body—VWR #34104-837/Orion #8175BN or VWR#10010-774/Orion #3175BNWP; or (ii) Orion PerpHect combination:VWR #34104-843/Orion #8203BN semi-micro, glass body; or (iii) suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149 g force). The pH is assessed in supernatant after one minute or the taking reading is stabilized. After each pH assessment, the electrode is washed with deionized water. Any excess water is wiped with a laboratory grade tissue. When not being used, the electrode is kept immersed in a pH 7 buffer solution or an appropriate electrode storage solution.

pH Modifying Agent

The dentifrice compositions herein may include an effective amount of a pH modifying agent, alternatively wherein the pH modifying agent is a pH buffering agent. pH modifying agents, as used herein, refer to agents that can be used to adjust the pH of the dentifrice compositions to the above-identified pH range. pH modifying agents may include alkali metal hydroxides, ammonium hydroxide, organic ammonium compounds, carbonates, sesquicarbonates, borates, silicates, phosphates, imidazole, and mixtures thereof. Specific pH agents include monosodium phosphate (monobasic sodium phosphate), trisodium phosphate (sodium phosphate tribasic dodecahydrate or "TSP"), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, phosphoric acid. In one embodiment, the dentifrice composition comprises: from 0.01% to 3%, preferably from 0.1% to 1% of TSP by weight of the composition; and from 0.001% to 2%, preferably from 0.01% to 0.3% of monosodium phosphate by weight of the composition. Without wishing to be bound by theory, TSP and monosodium phosphate may also have calcium ion chelating activity and therefore provide some monofluorophosphate stabilization (in those formulations containing monoflurophosphate).

Anti-Calculus Agent

The dentifrice compositions may include an effective amount of an anti-calculus agent, which in one embodiment may be present from about 0.05% to about 50%, by weight of the composition, alternatively from about 0.05% to about 25%, alternatively from about 0.1% to about 15% by weight of the composition. Non-limiting examples include those described in US 2011/0104081 A1 at paragraph 64, and those described in US 2012/0014883 A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably 0.01% to 2%, more preferably from 0.1% to 1% of the pyrophosphate salt by weight of the composition. Without wishing to be bound by theory, TSPP may provide not only calcium chelating thereby mitigating plaque formation, but also may provide the additional benefit of monofluorophosphate stabilization (in those formulations containing monofluorophosphate).

Surfactant

The dentifrice compositions herein may include a surfactant. The surfactant may be selected from anionic, nonionic, amphoteric, zwitterionic, cationic surfactants, or mixtures thereof. The composition may include a surfactant at a level of from about 0.1% to about 10%, from about 0.025% to about 9%, from about 0.05% to about 5%, from about 0.1% to about 2.5%, from about 0.5% to about 2%, or from about 0.1% to about 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraph 36; cationic surfactants may include those described at paragraphs 37 of the reference; and nonionic surfactants may include those described at paragraph 38 of the reference. In one embodiment, the composition comprises 0.1% to 5%, preferably 0.1% to 3%, alternatively from 0.3% to 3%, alternatively from 1.2% to 2.4%, alternatively from 1.2% to 1.8%, alternatively from 1.5% to 1.8%, alternatively combinations thereof, of the anionic surfactant sodium lauryl sulfate (SLS) by weight of the composition.

Thickening Agent

The dentifrice compositions herein may include one or more thickening agents. A thickening agent may be used in an amount from about 0.01% to about 15%, or from about 0.1% to about 10%, or from about 0.1% to about 5%, by weight of the composition. Non-limiting examples may include those described in US 2008/0081023 A1 at paragraphs 134 to 137, and the references cited therein.

In embodiment, the composition comprises a linear sulfated polysaccharide as a thickening agent. Carrageenans or carrageenins are one example of a linear sulfated polysaccharide. Generally, carrageenans can vary based upon the degree of sulfation that include: Kappa-carrageenan, Iota-carrageenan, and Lambda-carrageenan. Combinations of carrageenans can be used. In one embodiment, the composition contains from 0.1% to 3% of a linear sulfated polysaccharides by weight of the composition, preferably from 0.5% to 2%, alternatively from 0.6% to 1.8%, alternatively combinations thereof. In one embodiment, Iota-carrageenan is used.

In one embodiment, the composition comprises a silica agent, preferably a thickening silica obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167). In one embodiment, the composition comprising from 0.5% to 5% by weight of the composition of a silica agent, preferably from 1% to 4%, alternatively from 1.5% to 3.5%, alternatively from 2% to 3%, alternatively from 2% to 5%, alternatively from 1% to 3%, alternatively combinations thereof by weight of the composition.

In one embodiment, the composition comprises a carboxymethyl cellulose ("CMC"). CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A). In one embodiment, the composition contains from 0.1% to 3% of a CMC by weight of the composition, preferably from 0.5% to 2%, alternatively from 0.6% to 1.8%, alternatively combinations thereof by weight of the composition.

In yet another embodiment, the thickener agents may comprise liner sulfated polysaccharide (e.g., carrageenans), CMC, and preferably also a thickening silica for purposes of cost savings while achieving the right balancing of viscosity and elasticity. In one embodiment, the composition comprises a thickener comprising: (a) 0.01% to less than 1.4%, preferably from 0.1% to 1.3%, more preferably from 0.5% to 1.3% of a carrageenan by weight of the dentifrice composition; and (b) greater than 0.4-% to 2-%, preferably from 0.5% to 1.8%, more preferably from 0.6% to 1.8% of a carboxymethyl cellulose (CMC) by weight of the dentifrice composition. In yet another embodiment, the aforementioned thickener further comprises 0.5% to 5%, preferably 1% to 4%, of a thickening silica by weight of the dentifrice composition.

Low or Free Humectants

The compositions herein may be substantially free or free of humectants, alternatively contain low levels of humectants. The term "humectant," for the purpose of present invention, includes edible polyhydric alcohols such as glycerin, sorbitol, xylitol, butylene glycol, propylene glycol, and combinations thereof. In one embodiment, the humectant is selected from sorbitol, glycerin, and combinations thereof. In yet another embodiment, the humectant is sorbitol. In one embodiment, the composition comprises from 0% to less than 20% of humectants by weight of the composition, preferably from 0% to 10%, alternatively from 0% to 5%, alternatively from 0% to 3%, alternatively from 0% to 2%, alternatively from 0% to 1%, alternatively less than 20%, or less than 19%, 18%, 15%, 12%, 8%, 7%, 6%, 4%, 3%, 2%, 1%, or less than 0.5%; or greater than 1%, or greater than 2%, 5%, 10%, or 15%; or combinations thereof, by weight of the composition. In yet another embodiment, the composition contains less than 20% of sorbitol by weight of the composition.

In an alternative embodiment, the compositions of the present invention comprise a humectant, preferably from 1% to 15% by weight of the composition.

Colorant

The compositions herein may include a colorant. Titanium dioxide is one example of a colorant. Titanium dioxide is a white powder which adds opacity to the compositions. Titanium dioxide generally can comprise from about 0.25% to about 5%, by weight of the composition.

Flavorant

The compositions herein may include from about 0.001% to about 5%, alternatively from about 0.01% to about 4%, alternatively from about 0.1% to about 3%, alternatively from about 0.5% to about 2%, alternatively 1% to 1.5%, alternatively 0.5% to 1%, alternatively combinations thereof, of a flavorant composition by weight of the composition. The term flavorant composition is used in the broadest sense to include flavor ingredients, or sensates, or sensate agents, or combinations thereof. Flavor ingredients may include those described in US 2012/0082630 A1 at paragraph 39; and sensates and sensate ingredients may include those described at paragraphs 40-45, incorporated herein by reference. Excluded from the definition of flavorant composition is "sweetener" (as described above).

A. Data: Improved Antimicrobial Activity in Low or Nil Humectant Alkaline Dentifrice Compositions The antimicrobial activity is measured using the in vitro Plaque Glycolysis and Re-growth Model ("i-PGRM") such as described in U.S. Pat. No. 6,821,507, at col. 14, 1. 58 to col. 16, 1. 28; with modifications as herein described. The i-PGRM is a technique where plaque is grown from human saliva, and treated with agents designed to produce various levels of antimicrobial activity. The purpose of this technique is to provide a simple and quick method for determining if dentifrice compositions have a direct effect on the metabolic pathways that plaque microorganisms utilize for the production of toxins which adversely affect oral health. In particular, the model focuses on the metabolic production of organic acids including lactic, acetic, propionic, butyric acids and the decrease in pH caused by these acids. This method utilizes plaque grown on polished glass rods which are dipped in saliva overnight, soy broth and sucrose for 6 hours, and saliva again overnight. The plaque mass grown on the glass rods is then treated for 1 minute with supernatant of a weight ratio of 3:1 deionized water to dentifrice slurry, respectively. Supernatant is obtained by centrifuging the slurry at 13000 rpm (15871 relative centrifugal force (rcf)) for 10 minutes. The mass is then placed in a soy broth/sucrose solution for 6 hours and the pH of the incubation solution is measured at the end of the 6 hours. Thus, there are measures of pre-incubation pH and post incubation pH for both test formulations and controls. This testing is typically done with four replicates to minimize experimental variances, and a mean pH is calculated from these replicates.

The i-PGRM score is measured relative to a regular fluoridated formulation CREST® Cavity Protection, Lot Number 324931 ("Negative Control") and to a stannous fluoride containing formulation as "Positive Control" (stabilized stannous fluoride dentifrice as shown in Example 9—Positive Control). Preferably, the i-PGRM scores are significantly different from placebo controls and ideally similar to those provided by the stannous fluoride formulation proven to effectively inhibit acid production of plaque grown in the test. The i-PGRM score is calculated according to the formula:

$$i\text{-PGRM Score} = 100\% \times (\text{Test product mean pH} - \text{Negative control mean pH})(\text{Positive control mean pH} - \text{Negative control mean pH})$$

The mean pH values refer to incubation media pH's obtained following treatment and sucrose challenge. The negative control plaque samples produce large amounts of acid, and hence their pH values are lower than that of plaque samples treated with the positive control. The effectiveness of a formulation will ideally be comparable to the positive control, and hence an ideal i-PGRM score should approach 100%, i.e., no change in pH from the formulation pH to in vitro pH.

The formulations described in FIG. 1 as well as identified commercial products are tested according to the i-PGRM method herein described and summarized in Tables 1, 2, and 3.

TABLE 1

| No. | Formulation | SLS (wt %) | Humectant (wt %) | Formula pH | i-PGRM Score |
|---|---|---|---|---|---|
| 1 | Ex. 6 | 1.1 | Glycerin (45%) | 8.8 | 10.5 |
| 2 | Ex. 5 | 1.1 | Glycerin (17.5%) | 9.4 | 37.4 |
| 3 | Ex. 4 | 1.1 | Sorbitol (16.8%) | 9.4 | 47.6 |
| 4 | Ex. 7 | 2 | 0 | 7.8 | 62.6 |
| 5 | Ex. 1 | 1.1 | 0 | 9.4 | 101.4 |
| 6 | Negative Control [A] | 1.1 | Sorbitol (42%) | 7.1 | 0 |
| 7 | Positive Control (Ex. 8) | 1.1 | Sorbitol (38.8%) | 4.0 | 100 |

[A] CREST Cavity Protection, Lot Number 324931

Table 1 shows the inventive composition of Example 1 performed significantly better than controls and comparative examples. Notably Example 1 did not contain humectant (i.e., neither glycerin nor sorbitol) and is formulated at pH 9.4. In contrast, Examples 4, 5, 6, although at a relatively high formula pH, performed worse than the positive control by containing humectant. Although not containing humectant, Example 7 is formulated at pH 7.8 and performed worse than the positive control and inventive Example 1. Without wishing to be bound by theory, the results achieved by Example 1, at least in part, are because the inventive composition is free of humectant and have an alkaline pH.

Table 2 shows the inventive compositions of Example 1, 2, and 3 performed significantly better than the negative control and comparative examples.

TABLE 2

| No. | Formulation | SLS (wt %) | Humectant (wt %) | Formula pH | i-PGRM Score |
|---|---|---|---|---|---|
| 1 | Ex. 1 | 1.1% | 0 | 9.4 | 67 |
| 2 | Ex. 3 | 1.61% | 0 | 9.5 | 75 |
| 3 | Ex. 2 | 2.1% | 0 | 9.6 | 94 |
| 4 | Colgate Maximum Protection (Brazil)[A] | 2.1% | Sorbitol (10%), Glycerin (18%) | 9.8 | 36 |
| 5 | Negative Control [B] | 1.1% | Sorbitol (42%) | 7.1 | 0 |
| 6 | Positive Control (Ex. 8) | 1.1% | Sorbitol (38.8%) | 4.0 | 100 |

[A] "COLGATE Brazil-CaCO3" contains a calcium carbonate as well as at least some sorbitol and glycerin. Lot No.: EXP02152055BR12JH
[B] CREST Cavity Protection, Lot Number 324931.

The results of Table 2 indicate that the results are achieved independent of surfactant and surfactant level. Inventive Examples 1-3 each are free of humectant, contain sodium lauryl sulfate ("SLS") at varying levels, and have a relatively high formulation pH. Example 2, having the highest level of SLS of the three inventive examples, also contains 2 wt % polyethylene glycol PEG-600 (i.e., having a range of average molecular weight of 570 to 630 Daltons) to help keep the composition phase stable.

As indicated in i-PGRM results of Table 2, the inventive examples did almost as well as the positive control and significantly better than the negative control and the commercialized Brazilian product from COLGATE (containing calcium carbonate and humectants sorbitol and glycerin). Without wishing to be bound by theory, the results achieved by Examples 1-3 are because, at least in part, the inventive composition is free of humectant and that results are not attributable to surfactant.

B. Data: Improved Fluoride Uptake in Low/Nil Humectant Alkaline Dentifrice Compositions.

Data is provided to demonstrate the superiority of inventive Example 9 in fluoride uptake. The nil polyol humectant at pH 9.4 dentifrice formulation of Example 9 provides better results as compared to comparative Example 10 (at a lower pH). Control compositions 11 and 12 (Control E and F, respectively) are also provided. Table 3 below details the components of the four dentifrice compositions on a weight percentage (wt %) basis. Methods are described including determining Mean Fluoride Uptake. Lastly, data is presented in Tables 4a and 4b.

TABLE 3

| Components: (Wt %) | Ex 9 Inventive | Ex 10 Comparative | Ex 11 Control E | Ex 12 Control F |
|---|---|---|---|---|
| Water | 57.39 | 51.12 | 13.77 | 32.08 |
| Glycerin | 0 | 0 | 45 | 0 |
| Sorbitol | 0 | 0 | 0 | 16.8 |
| Sodium Caboxy-methyl Cellulose | 0.91 | 0.4 | 0.91 | 1.32 |
| Carrageenan | 1.2 | 1.4 | 1.2 | 0 |
| Thickener Silica | 2.62 | 0.5 | 2.62 | 3 |
| CaCO$_3$ | 32 | 42 | 32 | 42 |
| SLS | 1.1 | 2 | 1.1 | 2.1 |
| Tetra Sodium Pyrophosphate | 0.6 | 0 | 0.6 | 0 |
| Flavor | 0.85 | 1 | 0.85 | 0.85 |
| Sodium Mono-phosphate | 0.08 | 0 | 0.08 | 0.08 |
| Sodium Triphosphate | 0.42 | 0 | 0.42 | 0.42 |
| Sodium Saccharine | 0.25 | 0.48 | 0.25 | 0.25 |
| Sodium Mono-fluorophosphate | 1.1 | 1.1 | 1.1 | 1.1 |
| Methyl Paraben | 0.05 | 0 | 0.05 | 0 |
| Propyl Paraben | 0.05 | 0 | 0.05 | 0 |
| Total: | 100 | 100 | 100 | 100 |
| pH: | 9.4 | 8.2 | 9.4 | 8.8 |

Referring to Table 3, the inventive composition (Ex 9) notably contains 1.1% of sodium monoflurophosphate (MFP) by weight of the composition, nil glycerin and nil sorbitol, and is at pH 9.4. Comparative Example 10 notably also has MFP (1.1 wt %) and nil of the polyol humectants, but is at a lower pH of pH 8.2. Control E has MFP but 45% of glycerin by weight of the composition. Control F has MFP but has 16.8% of sorbitol by weight of the composition.

Analytical Methods

The method for assessing Mean Fluoride Uptake is described. Enamel specimens are prepared by cutting 4 mm cores (chips) from extracted, human maxillary incisors using a diamond core drill. Chips are mounted in ¼ inch diameter Lucite rods (Beijing Mengzhijie M&E Engineering Technology Co., Ltd.) with dental acrylic (Shanghai New Century Dental Materials Co., Ltd.) covering all sides except the lingual surface. Course polishing of the surface with 600 grit silicon carbide-water slurry is used to remove approximately 50 microns of the outer enamel. Specimens are then polished for 30 minutes with gamma alumina (40-10076, BUEHLER) to a mirror finish. After sonicating and rinsing with deionized water, each chip is exposed to 25 ml of demineralization solution (0.025M/L lactic acid, 2×10-4 MHDP (MethaneHydroxy Diphosphonate), pH 4.5) for 32 hours at 23° C. for the formation of initial carious lesions. After removal from the demineralization solution, the chips are carefully rinsed in deionized water. Each chip is assessed through visual inspection (10× magnifications) to ensure enamel is free of surface imperfections. Chips are randomly placed into treatment groups (at 5 chips per treatment group). Early carious lesion with slight mineral loss is necessary for the fluoride uptake test to assess the absorption of the fluoride ion.

Dentifrice treatments are prepared by thoroughly mixing 8 grams of the subject dentifrice sample with 24 g of fresh pooled human saliva to form a slurry. The saliva is utilized within 2 hours of collection. Slurries are centrifuged for 10 minutes at 10,000 rotations per minute (12,096 g) and the supernatant removed. Each treatment group of specimens is exposed to 20 ml of supernatant for 30 minutes with constant stirring with a magnetic stir bar. Following the treatment, specimens are thoroughly rinsed with deionized water and then analyzed for fluoride content. A microdrill biopsy technique is used to assess each dentifrice sample's ability to deliver fluoride to the demineralized enamel. Specimens are mounted on the microdrill stage and sampled using a modified carbide dental bur. The biopsy technique removes a small portion of the chip, leaving behind a cylinder with the approximate dimensions 30-50 μm diameter and a constant 50 μm height. The powder removed is dissolved in a 66.7 μl 0.5M HClO$_4$, then buffered and pH adjusted with 133.4 μl Total Ionic Strength Adjustment Buffer (e.g., TISAB II) and 0.5N NaOH solution (1:1 value ratio) resulting in a final volume of 200 μl. Sample solutions are then analyzed by reading the millivolt potential with a fluoride ion specific electrode (Orion, Model 9609BNWP). Fluoride concentration is determined from a commercially available standard fluoride calibration curve obtained on the same day as the analysis and then calculated and averaged to obtain the Mean Fluoride Uptake.

Data Tables 4a and 4b summarize the results obtained from measuring the Mean Fluoride Uptake in the identified examples and controls. The first column identifies the product name. Example 9 is an inventive compound whereas Example 10 is comparative compound. Controls as well as commercialized products are also tested. The second column identifies the humectant type and weight percentage (if any). Notably inventive Example 9 and comparative Example 10 do not contain any humectant. The third column identifies the fluoride source in the compositions as well as the concentration (parts per million (ppm)). The weight percentage of fluoride source in the commercial product can be inferred from the ppm levels indicated on the packaging. The Mean Fluoride Uptake is assessed per the method as previously described and the Standard Error of Mean (SEM). Lastly, the column labeled as "Statistic" designates whether any tested product is A, B, C, or D (with A as the highest performing sample and D as the lowest performing sample with respect to fluoride update). A Gate-keeper Tukey statistical pair-comparison analysis method is used to group treatments and assess the relevant Statistic.

In both tables, inventive Example 9 demonstrated that highest level of Mean Fluoride Uptake at 5.39 and 6.42 in Tables 4a and 4b, respectively. A "Statistic" of "A" is represented for the inventive composition, wherein as the control and commercialized compositions all had a lower Mean Fluoride Uptake value and a "Statistic" lower than A. Notably, a key difference between Example 9 and Example 10 is that the pH for the inventive composition is 9.4 while the comparative example is pH 8.2. Without wishing to be bound by theory, the higher pH led, at least in those compositions that are glycerol and sorbitol free, to a higher Mean Fluoride Update. Example 9 also performed better than those Control compositions having a polyol glycerin or sorbitol.

TABLE 4a

| Product Name | Humectant Type (Weight %) | Fluoride Source in Dentifrice Composition | Mean Fluoride Uptake ± (SEM) | Statistic |
|---|---|---|---|---|
| Ex. 9 | Nil | 1450 ppm Fluoride (Na-MFP), | 5.39 ± 0.16 | A |
| Ex. 10 | Nil | 1450 ppm Fluoride (Na-MFP) | 4.88 ± 0.16 | B |
| Control G[A] | Glycerin (~20%) | 1450 ppm Fluoride (0.76% w/w Na-MFP & 0.1% w/w NaF) | 4.65 ± 0.26 | B |
| Control I[B] | Glycerin (~18%) Sorbitol(~10%) | 1450 ppm Fluoride (Na-MFP) | 3.28 ± 0.21 | C |
| Control E (Ex. 3) | Glycerin (45%) | 1450 ppm Fluoride (Na-MFP) | 3.15 ± 0.08 | C |
| Control H- (placebo) | Nil | 0 ppm Fluoride | 2.56 ± 0.17 | D |

[A]COLGATE Maxima Protection Anticaries, Lot No.: EXP1213(L)1364MX1124.
[B]COLGATE Maxima Protection Anticaries, Lot No.: EXP02152055BR12JH.

TABLE 4b

| Product Name | Humectant Type (Weight %) | Fluoride Source in Dentifrice Composition | Mean Fluoride Uptake ± (SEM) | Statistic |
|---|---|---|---|---|
| Ex. 9 | Nil | 1450 ppm Fluoride (Na-MFP) | 6.42 ± 0.24 | A |
| Ex. 10 | Nil | 1450 ppm Fluoride (Na-MFP) | 4.88 ± 0.16 | B |
| Control F (Ex. 4) | Sorbitol (16.8%) | 1450 ppm Fluoride (Na-MFP) | 4.57 ± 0.27 | B |
| Control I[D] | Glycerin (~18%) Sorbitol (~10%) | 1450 ppm Fluoride (Na-MFP) | 4.31 ± 0.31 | B |
| Control H (placebo) | Nil | 0 ppm Fluoride | 3.0 ± 0.10 | C |

[D]COLGATE Maxima Protection Anticaries Lot No.: EXP02152055BR12JH (calcium carbonate based toothpaste).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
   (a) 45% to 75% water by weight of the composition;
   (b) 25% to 50% of a calcium-containing abrasive by weight of the composition; and
   (c) 0.0025% to 2% of sodium monofluorophosphate by weight of the composition;
   (d) from 0.01% to less than 1.4% carrageenan;
   (e) a pH modifying agent selected from the group consisting of alkali metal hydroxides, ammonium hydroxide, organic ammonium compounds, carbonates, sesquicarbonates, borates, silicates, phosphates, imidazole, and combinations thereof;
   (f) from 1% to 4% of a polyethylene glycol wherein the polyethylene glycol comprises an average molecular weight from 100 to 1600 Daltons;
   (g) said composition having a pH greater than 9; and
   wherein the composition is substantially free of a humectant selected from glycerin and sorbitol.

2. The composition of claim 1, wherein the composition is also substantially free of a polyol other than said glycerin or sorbitol.

3. A composition according to claim 1 wherein the abrasive is calcium carbonate.

4. The composition of claim 1 further comprising 0.01% to 0.11 by weight of a paraben.

5. The composition of claim 4, wherein the paraben is selected from methyl paraben, propyl paraben, or combinations thereof.

6. A dentifrice composition according to claim 5 further comprising:
   27% to 37% of a calcium-containing abrasive by weight of the composition;

from 0.5% to 1.3% of a carrageenan by weight of the composition;

from 0.6% to 1.8% of a carboxymethyl cellulose (CMC) by weight of the composition.

7. The composition of claim 6, further comprising 0.5% to 5% of a thickening silica by weight of the composition.

8. The composition of claim 6 further comprising from 0.5% to 1.5% by weight of sodium monofluorophosphate.

9. The composition of claim 6, further comprising 0.1% to 12% by weight of sodium lauryl sulfate.

10. A method of treating tooth enamel comprising the step of brushing teeth with a dentifrice composition of claim 1.

11. A method of mitigating plaque formation on tooth enamel comprising the step of brushing teeth with a dentifrice composition of claim 6.

12. The composition of claim 1 comprising from 50% to 70%, by weight of the composition, water.

13. The composition of claim 12 comprising from 55% to 65%, by weight of the composition, water.

14. The composition of claim 1 wherein the pH is 9.4 to 9.6.

15. The composition of claim 1 wherein the pH is 9.4.

16. A dentifrice composition comprising:
(a) 50% to 60% water by weight of the composition;
(b) 27% to 37% of a calcium-containing abrasive by weight of the composition; and
(c) 0.0025% to 2% of sodium monofluorophosphate by weight of the composition;
(d) from 0.6% to less than 1.8% carrageenan;
(e) from 2% to 9% of an anionic surfactant;
(f) a pH modifying agent selected from the group consisting of alkali metal hydroxides, ammonium hydroxide, organic ammonium compounds, carbonates, sesquicarbonates, borates, silicates, phosphates, imidazole, and combinations thereof;
(g) said composition having a pH from 9 to 10; and wherein the composition is substantially free of a humectant selected from glycerin and sorbitol.

17. A dentifrice composition comprising:
(a) 50% to 60% water by weight of the composition;
(b) 27% to 37% of a calcium-containing abrasive by weight of the composition; and
(c) 0.0025% to 2% of sodium monofluorophosphate by weight of the composition;
(d) from 0.6% to less than 1.8% carrageenan;
(e) from 2% to 9% of an anionic surfactant;
(f) from 1% to 3% of a polyethylene glycol wherein the polyethylene glycol comprises an average molecular weight from 400 to 800 Daltons;
(f) a pH modifying agent selected from the group consisting of alkali metal hydroxides, ammonium hydroxide, organic ammonium compounds, carbonates, sesquicarbonates, borates, silicates, phosphates, imidazole, and combinations thereof;
(g) said composition having a pH from 9 to 10; and wherein the composition is substantially free of a humectant selected from glycerin and sorbitol.

* * * * *